United States Patent [19]

Kim et al.

[11] Patent Number: 5,571,770
[45] Date of Patent: Nov. 5, 1996

[54] CATALYST FOR FLUORINATION OF 1,1,1,-TRIFLUORO-2,2-DICHLOROETHANE AND METHOD FOR PREPARING THE SAME

[75] Inventors: Hoon Sik Kim; Moon Jo Chung; Byung Gwon Lee; Hyun Joo Lee, all of Seoul, Rep. of Korea

[73] Assignee: Korea Institute of Science and Technology, Seoul, Rep. of Korea

[21] Appl. No.: 490,726

[22] Filed: Jun. 15, 1995

[30] Foreign Application Priority Data

Dec. 2, 1994 [KR] Rep. of Korea ............... 32574/1994

[51] Int. Cl.$^6$ ........................................ B01J 23/26
[52] U.S. Cl. ................. 502/307; 502/305; 502/306; 502/317
[58] Field of Search ......................... 502/305, 306, 502/307, 319; 570/166, 168, 169

[56] References Cited

U.S. PATENT DOCUMENTS

| | | |
|---|---|---|
| 3,258,500 | 6/1966 | Swamer et al. |
| 3,978,145 | 8/1976 | Knaak ............... 260/653.6 |
| 3,992,325 | 11/1976 | Knaak ............... 252/442 |
| 4,843,181 | 6/1989 | Gumprecht et al. |
| 5,281,568 | 1/1994 | Scott et al. ............... 502/307 |
| 5,449,656 | 9/1995 | Scott et al. ............... 502/307 |

FOREIGN PATENT DOCUMENTS 4-29940  1/1992  Japan.

*Primary Examiner*—Anthony Mc Farlane
*Assistant Examiner*—Alexander G. Ghyka
*Attorney, Agent, or Firm*—Darby & Darby, P.C.

[57] ABSTRACT

There are a catalyst for fluorination production of 1,1,1-trifluoro-2,2-dichloroethane comprises chromium, one compound selected from the group consisting of Mg and Ca and at least one metal component selected from the group consisting of Zn, Ce and Ni, wherein the molar ratio of Cr to Mg or Ca ranges from 1:1 to 1:32 and the molar ratio Cr to the metal component is not more than 1:0.5, and method for preparing the same comprising the steps of; producing an admixture of a composition comprising chromium, one compound selected from the group consisting of magnesium fluoride and calcium fluoride and at least one metal compound selected from a group consisting of cerium fluoride, zinc fluoride and nickel fluoride with water and refluxing the admixture in methanol or ethanol.

7 Claims, No Drawings

CATALYST FOR FLUORINATION OF 1,1,1,-TRIFLUORO-2,2-DICHLOROETHANE AND METHOD FOR PREPARING THE SAME

BACKGROUND OF THE INVENTION

1. Field of the Invention

The present invention relates to a catalyst for fluorination of 1,1,1-trifluoro-2,2-dichloroethane and more particularly, to a catalyst for producing pentafluoroethane from 1,1,1-trifluoro-2,2-dichloroethane, significantly improved in durability, selectivity and activity and a method for the preparation of the catalyst.

2. Description of the Prior Art

R-502 (a mixture of CFC-115 ($CF_3CF_2Cl$) and CFC-22 ($CHF_2Cl$)) has been one of the most important cooling agents utilized extensively in refrigerators, automobile cooling systems, and various other related industries because it is harmless to! the human body and superior in thermodynamic physical properties.

However, intensive research and observation has revealed that CFC-115 is a main substance that destroys the ozone layer in the stratosphere. According to the Montreal protocol internationally agreed in 1987, it is prescribed that CFC-115 should be prohibited from production and use starting from 1996.

Pentafluoroethane ($CF_3CHF_2$: hereinafter referred to as "HCFC-125"), one of important substitutients for R-502 has similar physical properties to R-502 when it is used with HFC-32 ($CH_2CF_2$), HFC-143a ($CF_3CH_3$) or HFC-134a ($CF_3CH_2F$) as well as does little damages to the ozone layer and has a much less influence to the earth's greenhouse effect.

HCFC-125 may be produced by reacting various $C_2$ compounds with HF, for example, by reacting HCFC-123 ($CF_3CHCl_2$) with HF as shown in the following reaction formula:

$$2\ CF_3CHCl_2 + 3\ HF \rightarrow CF_3CHClF + CF_3CHF_2 + HCl$$

In the above reaction, though 1,1,1,2-tetrafluoro-2-chloroethane ($CF_3CHClF$: hereinafter referred to as "HCFC-124") is also produced, it is removed and can be fluorintated to HCFC-125.

However, it is known that the substitution of fluorine for chlorine in HCFC-123 is a very difficult reaction. Thus, an effective catalyst is required to promote this reaction. As previously known, chromium oxide (III) ($Cr_2O_3$)-containing catalyst is effective for the partial fluorination reaction. In many a patent, techniques for the preparation of a chromium oxide-containing catalyst are disclosed.

Chromium oxide (III) catalysts developed thus far, however, include many disadvantages that need to be improved, such as catalyst life span and selectivity. For example, since the partial fluorination reaction proceeds at high temperatures, e.g. above 350° C., organic compounds, a reactant for the partial fluorination reaction or a product of the reaction, are decomposed to deposit carbons on the catalyst. As a result, the catalyst is deactivated at a rapid rate.

In order to retard the deactivation rate of the catalyst, a process of supplying oxygen together with the reactants has been reported. However, this process does not completely prevent the deactivation of the catalyst. In addition, the supplied oxygen oxidizes the HCl resulted from the partial fluorination reaction to generate a chlorine gas and water. The generated chlorine gas, in turn, reacts with the reactants to yield many by-products for example, CFC-113 ($CF_3ClCFCl_2$), CFC-114 ($CF_2ClCF_2Cl$) and CFC-115 ($CF_3CF_2Cl$) which make the separation and filtration of HCFC-125 or HCFC-124 difficult. The water by-produced is acidified by dissolving the coexisting HCl and HF in a reactor. The acid solution causes corrosion of the equipment including the reactor, and thus has a serious effect on the durability of the equipment.

Many methods for preparing HCFC-124 or HCFC-125 from fluorination reaction in the presence of chromium oxide catalyst have been developed. For example, U.S. Pat. No. 3,258,500 discloses a method for fluorinating tetrachloroethylene in the presence of alumina-supported chromium oxide catalyst at the temperature of 400° C. In this method, however, the selectivity of HCFC-123, HCFC-124 and HCFC-125 is at most 3.5%, 9.2% and 35.5%, respectively.

In U.S. Pat. No. 4,843,181, a method for fluorinating tetrachloroethylene using chromium oxide catalyst obtained by pyrolyzing ammonium dichromate at 500° to 650° C. is suggested. In this method, the total selectivity of HCFC-123, HCFC-124 and HCFC-125 is merely in the range of 71.1~90.07%.

Japanese Laid-Open publication No. 4-29940 suggests a method for producing HCFC-123, HCFC-124 and HCFC-125 from HCFC-122 ($CF_2ClCHCl_2$) in the presence of alumina containing chromium catalyst with supply of oxygen. Although the total selectivity of HCFC-123, HCFC-124 and HCFC-125 is about 99%, the starting material, HCFC-122 is expensive and has difficulty in producing itself.

SUMMARY OF THE INVENTION

The object of the present invention is to provide a catalyst for fluorination of 1,1,1-trifluoro-2,2-dichloroethane (HCFC-123), superior in selectivity and durability.

It is another object of the present invention to provide a method for the preparation of the catalyst, advantageous from an economic point of view.

The catalyst according to the present invention comprises chromium, one compound selected from the group consisting of Mg and Ca and at least one metal component selected from the group consisting of Zn, Ce and Ni wherein the molar ratio of Cr to Mg or Ca ranges from 1:1 to 1:32 and the molar ratio Cr to the metal component is not more than 1:0.5.

The catalyst, in accordance with the present invention, can be prepared by a method comprising the steps of: producing an admixture of a composition comprising chromium oxide, one compound selected from the group consisting of magnesium fluoride or calcium fluoride and at least one metal compound selected from the group consisting of cerium fluoride, zinc fluoride and nickel fluoride with water wherein the molar ratio of Cr to Mg or Ca ranges from 1:1 to 1:32 and the molar ratio Cr to the metal component is not more than 1:0.5; heat-refluxing the admixture with metanol or ethanol.

These and other objects and advantages of the present invention will become more apparent in the following description.

DETAILED DESCRIPTION OF THE INVENTION

In the catalyst of the present invention, the molar ratio of Cr to Mg or Ca is suitably present in the range of 1:1 to 1:32 and preferably 1:4 to 1:16.

The molar ratio of Cr to the metal components of the aqueous metal salt solution is not more than 1:0.5 and preferably in the range of 1:0.05 to 1:0.25. In the present invention, at least a metal component selected from the group consisting of cerium, zinc or nickel may be used.

The catalyst according to the present invention has wider surface area at the above of 130 $m^2/g$ comparing to 50 $m^2/g$ of the conventional chromium oxide catalyst. The wider surface area of the present catalyst makes the active component of the catalyst uniformly distributed in the catalyst, and increases effective area to catalyst fluorination reaction.

For the preparation of the catalyst according to the present invention, chromium oxide, magnesium fluoride or calcium fluoride and at least one metal compound selected from group consisting of cerium fluoride, zinc fluoride and nickel fluoride in a predetermined molar ratio are added in water. The mixture is refluxed with alcohol such as metanol and ethanol at the temperature of 50°–120° C. for hours. After the reaction is completed, the precipitate is removed and dried. The dried catalyst can be used itself, and if necessary, it can be used after sintering.

Herein, the terms "conversion" and "selectivity" are defined as follows:

$$\text{Conversion } HCFC\text{-}123(\%) = \frac{\text{amount of } HCFC\text{-}123 \text{ reacted}}{\text{amount of } HCFC\text{-}123 \text{ supplied}} \times 100$$

$$\text{Selectivity for } HCFC\text{-}124(\%) = \frac{\text{amount of } HCFC\text{-}124 \text{ produced}}{\text{amount of } HCFC\text{-}123 \text{ reacted}} \times 100$$

$$\text{Selectivity for } HCFC\text{-}125(\%) = \frac{\text{amount of } HCFC\text{-}125 \text{ produced}}{\text{amount of } HCFC\text{-}123 \text{ reacted}} \times 100$$

$$\text{Yield of } HCFC\text{-}125(\%) = \frac{\text{amount of } HCFC\text{-}125 \text{ produced}}{\text{amount of } HCFC\text{-}123 \text{ supplied}} \times 100$$

The catalyst of the present invention is superior in the conversion of the starting material, HCFC-123 and in the selectivity of HCFC-125. In addition, the conversion of the catalyst is maintained even after being used for a long period of time.

Since the activity of the catalyst of the present invention is maintained even after being used for a long period of time, it is unnecessary to supply oxygen during fluorinating reaction which is required to slow down the rapid inactivation of conventional catalysts in the reaction. Furthermore, no supply of oxygen to the reactants can bring about a great reduction in the generation of by-products. Accordingly, the separation of a desirable product from a mixture of the products of the catalytic reaction can be carried out in ease.

In addition, since no oxygen is supplied, unnecessary oxidation of HCl does not occur and only a very small amount of water is present in the system, which results in lowering the corrosion rate of the equipment used in the fluorination.

The preferred embodiments of the present invention will now be further described with reference to specific examples.

While specific embodiments of the invention have been described in considerable detail, variations and modifications of these embodiments can be effected without departing from the spirit and scope of the invention as described and claimed.

EXAMPLE 1

Preparation of the Catalyst 100 g of $CrO_3$, 248 g of $MgF_2$ and 6.5 g of $ZnF_2$ were mixed with 500 ml of water. The obtained admixture was reacted with 100 g of ethanol at the temperature of 60°–100° C., and boiled under reflux for a period of 16 hours. Afterwards the product was filtered and dried at 140° C. for 6 hrs. The dried product was formed into a cylindrical pellet with a size of 4 mm×4 mm. The surface area of the product was measured by BET method using AUTO SORB-1 (Quantachrome, U.S.A.). The result is shown in the following Table 1.

EXAMPLE 2

Preparation of the Catalyst

Catalyst was prepared in a manner similar to that of Example 1, except that metanol was used instead of ethanol.

EXAMPLES 3–8

Preparation of the Catalysts

Catalysts were prepared in a manner similar to that of Example 1, except that the compositions and their molar ratios were as shown in the following Table 1.

TABLE 1

| | Composition of the Catalysts | |
|---|---|---|
| Example No. | Composition of Catalyst (molar ratio) | surface area ($m^2/g$) |
| 1 | Cr:Mg:Zn = 1:4:0.06 | 162 |
| 2 | Cr:Mg:Zn = 1:4:0.06 | 158 |
| 3 | Cr:Mg:Ce = 1:4:0.05 | 147 |
| 4 | Cr:Mg:Ni = 1:1:0.10 | 132 |
| 5 | Cr:Mg:Zn = 1:16:0.05 | 173 |
| 6 | Cr:Mg:Ni = 1:32:0.25 | 188 |
| 7 | Cr:Mg:Ce:Zn = 1:8:0.1:0.1 | 165 |
| 8 | Cr:Mg:Zn:Ni = 1:4:0.1:0.05 | 134 |

EXAMPLES 9–14

Preparation of the Catalysts

Catalysts were prepared in a manner similar to that of Example 1, except that the compositions and their weight ratios were as shown in the following Table 2.

TABLE 2

| | Composition of the Catalysts | |
|---|---|---|
| Example No. | Composition of Catalyst (molar ratio) | surface area ($m^2/g$) |
| 9 | Cr:Ca:Ce = 1:4:0.05 | 144 |
| 10 | Cr:Ca:Ni = 1:1:0.10 | 130 |
| 11 | Cr:Ca:Zn = 1:16:0.05 | 168 |
| 12 | Cr:Ca:Ni = 1:32:0.25 | 181 |
| 13 | Cr:Ca:Ce:Zn = 1:8:0.1:0.1 | 159 |
| 14 | Cr:Ca:Zn:Ni = 1:4:0.1:0.05 | 131 |

EXAMPLE 15

Production of HCFC-124 and HCFC-125

30 g of the pelletized catalyst prepared in Example 1 was charged in a cylindrical reactor having a diameter of 2.54 cm and a length of 30 cm made of Inconel-600 tube (trade name), and slowly heated up to 400° C. with supplying nitrogen gas at a rate of 50 ml/min, so as to remove trace water therefrom.

The reactor was cooled to 200° C. and HF was passed through it. During passing the HF, the reactor was heated to 340° C. and HCFC-123 was supplied to it in such an amount as to make the mole ratio of HCFC-123 to HF 1:8. The contact time of HF with HCFC-123 was 10 seconds. HF and HCFC-123 were preheated up to 200° C. before introducing to the reactor. The obtained products were washed with MgO suspension and water to remove HF and HCl, and then collected at −60° C. The obtained mixture was analyzed using a gas chromatograph equipped with a Porapak-N column.

The conversion of HCFC-123 and the selectivity for HCFC-124 and the selectivity for HCFC-125 are shown in the following Table 3.

EXAMPLES 16–22

Production of HCFC-124 and HCFC-125

HCFC-125 was prepared in a manner similar to that of Example 15, except that the catalysts prepared in Examples 2 to 8 were used, respectively, and that the reaction temperatures, the mole ratios of HF/HCFC-133a and the contact times were as shown in the Table 3.

The conversion of HCFC-123a and the selectivities for HCFC-124 and HCFC-125 are given as shown in the following Table 3.

TABLE 3

| Exam. No. | Catalyst Source | Temp. (°C.) | HF/HCFC-123 (mol. ratio) | Time (sec) | Conversion HCFC-123 | Select. HCFC-125 | Select. HCFC-124 |
| --- | --- | --- | --- | --- | --- | --- | --- |
| 15 | Exam. 1 | 340 | 8  | 10 | 96.5  | 83.8 | 5.9  |
| 16 | Exam. 2 | 380 | 10 | 5  | 100.0 | 94.5 | 4.2  |
| 17 | Exam. 3 | 250 | 4  | 30 | 34.8  | 19.8 | 80.2 |
| 18 | Exam. 4 | 300 | 15 | 15 | 71.4  | 55.4 | 44.5 |
| 19 | Exam. 5 | 320 | 15 | 20 | 82.6  | 69.3 | 30.7 |
| 20 | Exam. 6 | 360 | 20 | 10 | 98.3  | 91.9 | 7.2  |
| 21 | Exam. 7 | 280 | 8  | 5  | 52.8  | 38.6 | 61.4 |
| 22 | Exam. 8 | 330 | 8  | 10 | 79.6  | 68.6 | 30.3 |

EXAMPLES 23–28

Production of HCFC-124 and HCFC-125

HCFC-125 was prepared in a manner similar to that of Example 15, except that the catalysts prepared in Examples 9 to 14 were used, respectively, and that the reaction temperatures, the mole ratios of HF/HCFC-133a and the contact times were as shown in the Table 4. The conversions of HCFC-133a and the selectivities for HCFC-124 and HCFC-125 are given as shown in the following Table 4.

TABLE 4

| Exam. No. | Catalyst Source | Temp. (°C.) | HF/HCFC-123 (mol. ratio) | Time (sec) | Conversion HCFC-123 | Select. HCFC-125 | Select. HCFC-124 |
| --- | --- | --- | --- | --- | --- | --- | --- |
| 23 | Exam. 9  | 380 | 10 | 5  | 100.0 | 92.7 | 4.8  |
| 24 | Exam. 10 | 250 | 4  | 30 | 32.6  | 17.7 | 82.3 |
| 25 | Exam. 11 | 300 | 15 | 15 | 70.4  | 52.3 | 47.7 |
| 26 | Exam. 12 | 320 | 15 | 20 | 79.7  | 68.8 | 31.3 |
| 27 | Exam. 13 | 360 | 20 | 10 | 97.2  | 89.2 | 9.9  |
| 28 | Exam. 14 | 280 | 8  | 5  | 50.3  | 34.8 | 65.2 |

EXAMPLE 29

Measurement of Catalyst Deactivation

To ascertain the deactivation of the catalyst when it is used for a long period of time without supply of oxygen, the yield of HCFC-125 was measured under the same conditions as Example 1. The yield of HCFC-125 was 80.9 % at the begining of the reaction and it was 79.8 % after 200 hours.

COMPARATIVE EXAMPLE 1

The catalyst according to U.S. Pat. No. 4,843,181 was prepared by pyrolyzing ammonium dichromate at 500° to 650° C. To ascertain the deactivation of the catalyst, the yield of HCFC-125 was measured at the begining of the reaction and after 200 hours under the same conditions as Example 1. The yield of HCFC-125 at the begining of the reaction was 81.6%, and it decreased to 54.2% 200 hours later.

What is claimed is:

1. A catalyst for the fluorination of 1,1,1-trifluoro-2,2-dichloroethane comprises chromium, one compound selected from the group consisting of Mg and Ca and at least one metal component selected from the group consisting of Ce, Zn and Ni, wherein the molar ratio of Cr to Mg or Ca ranges from 1:1 to 1:32 and the molar ratio Cr to the metal component is not more than 1:0.5.

2. The catalyst in accordance with claim 1, wherein said molar ratio of Cr to Mg or Ca ranges from 1:4 to 1:16.

3. The catalyst in accordance with claim 1, wherein said molar ratio of Cr to the metal component ranges from 1:0.05 to 1:0.25.

4. The catalyst in accordance with claim 1, wherein the surface of the catalyst is more than 130 m$_2$/g.

5. A method for preparing a catalyst for fluorination of 1,1,1-trifluoro-2,2-dichloroethane comprising the steps of:

producing an admixture of a composition comprising chromium, one compound selected from the group consisting of magnesium fluoride and calcium fluoride and at least one metal compound selected from the group consisting of cerium fluoride, zinc fluoride and nickel fluoride with water wherein the molar ratio of Cr to Mg or Ca ranges from 1:1 to 1:32 and the molar ratio Cr to the metal component is not more than 1:0.5; and refluxing the admixture in methanol or ethanol.

6. The method in accordance with claim 4, wherein said molar ratio of Cr to Mg or Ca ranges from 1:4 to 1:16.

7. The method in accordance with claim 5, wherein said molar ratio of Cr to the metal component ranges from 1:0.05 to 1:025.

* * * * *